United States Patent [19]

Ravdin et al.

[11] Patent Number: 5,004,608

[45] Date of Patent: Apr. 2, 1991

[54] AMEBIASIS VACCINE

[75] Inventors: Jonathan I. Ravdin, Earlysville; William A. Petri, Jr., Palmyra, both of Va.

[73] Assignee: The University of Virginia Alumni Patents Foundation, Charlottesville, Va.

[21] Appl. No.: 456,579

[22] Filed: Dec. 29, 1989

Related U.S. Application Data

[63] Continuation of Ser. No. 143,626, Jan. 13, 1988, abandoned.

[51] Int. Cl.$^5$ ............... A61K 39/02; A61K 39/00
[52] U.S. Cl. ............................ 424/88; 424/92; 424/93; 530/396
[58] Field of Search ................ 530/396; 424/88, 92, 424/93

[56] References Cited

PUBLICATIONS

Petri; W., Infection and Immunity, Oct. 1987, vol. 55, No. 10, pp. 2327-2331.
Petri; W., J. Clin. Invest., vol. 80, Nov. 1987, 1238-1244.
Ravdin; J., J. Clin. Invest., vol. 68, Nov. 1981, 1305-1313.
Ravdin; J., The Journal of Infectious Disease, vol. 151, No. 5, May 1985, p. 804.
Sharma; A., Int. J. Immunopharmac., vol. 6, No. 5, pp. 483-491, 1984.
Sharma; A., Infection and Immunity, Jun. 1985, pp. 634-637.
Kobiler; D., Infection and Immunity, vol. 29, No. 1, pp. 221-225, Jul. 1980.
Moss; B., Nature, vol. 311, Sep. 6, 1984, p. 67.
Petri et al., "Pathogenic and Nonpathogenic Strains of *Entamoeba histolytica* Can Be Differentiated by Monoclonal Antibodies to the Galactose-Specific Adherence Lectin", Infection and Immunity, 58:6, pp. 1802-1806 (U.S.A. 1990).
Petri et al., "Monoclonal Antibodies Directed Against the Galactose-Binding Lectin of *Entamoeba histolytica* Enhance Adherence", The Journal of Immunology, 144:12, pp. 4803-4809 (U.S.A. 1990).
Ravdin et al., The Role of Adherence on Cytopathogenic Mechanisms of *Entamoeba histolytica*, Study with Mammalian Tissue Culture Cells and Human Erythrocytes, J. Clin Invest, 68:1305-1313 (1981), U.S.A.
Ravdin et al., N-Acetyl-D-Galactosamine inhibitable Lectin of *Entamoeba histolytica*, I. Partial Purification and Relations to Amoebic in vitro, J.Infect Dis, 151: 804-815 (1985), U.S.A.
Salata et al., The N-Acetyl-D-Galactosamine Inhibitable Lectin of *Entamoebia histolytica*, II, Mitogenicity for Human Lymphocytes, J. Infect Dis, 151: 816-822 (1985), U.S.A.
Ravdin et al., Adherence of *Entamoeba histolytica* Trophozoites to Rat and Human Colonic Mucosa., Infect Immun, 48:292-297 (1985), U.S.A.
Ravdin, J. I., Pathogenesis of Disease Caused by *Entamoeba histolytica*: Studies of Adherence, Secreted Toxins, and Contact-Dependent Catalysis, Rev Infect Dis, 8:247-260 (1986), U.S.A.
Salata et al., Patients Treated for Amebic Liver Abscess Develop Cell-Mediated Immune Responses Effective in vitro Against *Entamoeba histolytica*, J. Immunol, 136: 2633-2639 (1986), U.S.A.
Salata et al., Review of the Human Immune Mechanisms Directed Against *E. histolytica*, Rev Infect Dis, 8:261-272 (U.S.A.) (1986).
Salata et al., The Interaction of Human Neutrophils and *Entamoeba histolytica* Trophozoites Increases Cytopathogenicity for Liver Cell Monolayers, J Infect Dis, 154:19-26 (1986), U.S.A.
Ravdin et al., Production of Mouse Monoclonal Antibodies which Inhibit in vitro Adherence of *Entamoeba histolytica* Trophozoites, Infect Immun, 53:1-5 (1986), U.S.A.
Petri et al., Characterization of the Membrane and Soluble Forms of the Adherence Lectin of *Entamoeba histolytica*, Abstract #41, Presented Dec. 8-11 (1986), Denver, Colo.
Petri et al., Adherence Mechanisms of *Entamoeba histolytica*: The N-Acetyl-D-Galactosamine Inhibitable Lectin, Clin Res, 34:222A (1986), U.S.A.
Petri et al., Isolation of the Adherence Lectin of *Entamoeba histolytica*, Clin Res, 34:529A (1986), U.S.A.
Chadee et al., Binding of Purified Rat Colonic Muchs to the Gal/GalNAc Adherence Lectin of *Entamoeba histolytica*, Clin Res, 34:438A (1986), U.S.A.

Primary Examiner—Howard E. Schain
Assistant Examiner—Choon P. Koh
Attorney, Agent, or Firm—James Creighton Wray

[57] ABSTRACT

Purified Gal/GalNAc adherence lectin of *Entamoeba histolytica* is used for development of a vaccine to prevent human amebiasis.

5 Claims, No Drawings

AMEBIASIS VACCINE

This application is a continuation, of U.S. patent application Ser. No. 143,626, filed Jan. 13, 1988.

This invention relates to the control and reduction of human disease due to the protozoan parasite *Entamoeba histolytica*, which are parasitic amoebas of vertebrates which cause breakdown of body tissue. Amoebas are a large genus of naked rhizopod protozoans.

Currently, 10% of the world's population is infected with *E. histolytica*. Worldwide there are 50,000,000 cases of invasive amebiasis resulting in 50 to 100 thousand deaths per annum. Amebiasis is a disease or infection caused by amoebas.

At present, there is no vaccine available to prevent invasive amebiasis. The molecule responsible for adherence of the parasite to tissue was not previously described.

The present invention provides isolated lectin for use as a vaccine for prevention of amebiasis and also for use in diagnosis of virulent amebiasis.

Purified Gal/GalNAc adherence lectin of *Entamoeba histolytica* is used for development of a vaccine to prevent human amebiasis.

We have isolated and described the galactose binding lectin of *Entamoeba histolytica* which mediates the adherence of the parasite to mammalian and human cells (Clin Res 34:222A, 1986 and 34:529A, 1986; Petri et al, J Clin Invest 80:1238-44, 1987, attached). Immunization with this newly purified lectin protein as a vaccine or for the development of a recombinant DNA vaccine for prevention of human invasive amebiasis is the present invention.

Ravdin and co-workers have established that adherence of axenic *E. histolytica* to trophozoites of Chinese hamster ovary (CHO) cells, human erythrocytes and white blood cells, fixed rat and human colonic mucosa, rat colonic submucosa, purified rat and human colonic mucus, and rat colonic epithelial cells is mediated by a galactose inhibitable lectin on the surface of the parasite (J Clin Invest 68:1313, 1981; J Infect Dis 151:804, 1985; Infect Immun 48:292, 1985; J Clin Invest 76:481, 1985; Infect Immun 53:1, 1986; Clin Res 34:438A, 1986, J Clin Invest 80:1245-54, 1987). Bracha and Mirelman (1982, 1983) demonstrated that the parasite's galactose inhibitable lectin mediated its adherence to opsonized bacteria or bacteria containing galactose or GalNAc residues in its lipopolysaccharide. Inhibition of parasite adherence prevents lysis of the target cells (J Exper Med 152:377, 1980; J Clin Invest 68:1313, 1981). The in vivo and in vitro virulence of different strains of *E. histolytica* correlates directly with their amount of lectin activity per mg of amebic protein (J Infect Dis 151:804, 1985) and adherence dificient *E. histolytica* clones are avirulent (Orozco, Rodriquez, Salata, Murphy, Ravdin—Exp. Parasit. 63:157, 1987. Therefore, we have ample evidence to conclude that the parasite's galactose inhibitable adherence lectin is absolutely essential for virulence; inhibition of the function of this parasite protein by using a vaccine composed of the adherence lectin or portions of the lectin in a recombinant DNA vaccine should prevent disease due to *E. histolytica*.

We have recently isolated and described this lectin (Petri et al., J Clin Invest 80:1238-44.) The adherence lectin was purified by galactose-affinity chromatography and with adherence-inhibitory monoclonal antibodies. Monoclonal antibodies which inhibited amebic adherence exclusively recognized the denatured or native 170K dalton amebic protein isolated by galactose affinity chromatography; seven additional anti-*E. histolytica* monoclonal antibodies which do not inhibit adherence did not recognize the lectin. Indirect immunofluorescence with monoclonal antibody designated F-14, which inhibits amebic adherence by 86% confirmed the surface location of the lectin. The lectin molecule is a glycoprotein as determined by metabolic labeling with (3H) glucosamine and by concanavaline A binding. (Petri & Ravdin, unpublished results.) The lectin is antigenic; it was recognized on Western blots by human immune sera obtained from patients treated for liver abscess (Petri et al Infect Immun 55:2327-2331, 1987.) We have sequenced the first 15 amino-terminil amino acids of the adherence lectin. Search of the NBRF library revealed no homologous sequence in any other protein that has been sequenced to date (Petri & Ravdin, unpublished).

In summary, we have the first to isolate the adherence lectin of *Entamoeba histolytica*. We have ample evidence that this amebic molecule is absolutely essential for parasite pathogenicity. Eliciting a host immune response by immunization with this amebic protein should provide immunity against invasive amebiasis. Immunization with all or a portion of the lectin molecule may be optimal. The specific anti-lectin mouse monoclonal or rabbit polyclonal antibodies produced by the purified lectin can be utilized to screen a cDNA expression library for the lectin protein. Insertion of the lectin encoding DNA into a DNA virus vector such as vaccinia virus (by the method of Moss et al Nature 311:67 (1984)), and immunization with this recombinant virus or oral immunization of attenuated *Salmonella dublin* bacteria constitutively producing recombinant amebic lectin are alternate methods for use of the purified lectin and the DNA encoding the lectin in development of a vaccine against amebiasis.

In one example, a lectin protein of *E. histolytica* is purified as above described. The purified lectin protein is injected in a host. An immune reaction is elicited in the host which produces antibodies against the particular lectin protein. When amoebas within an alimentary system of a host produce the particular lectin protein, the host's antibodies attach the lectin protein and reduce it or render the particular lectin protein inoperative, thus preventing attachment or maintenance of the amoebas within the host.

In another example, a portion of the lectin protein molecule is separated from a remaining portion and one of the portions is injected as a vaccine to elicit production of antibodies by the host.

In another example, the DNA gene encoding the amebic lectin is inserted into attenuated *Salmonella dublin*. The lectin is gene is fused to the LT-B toxin of *E. coli* on a plasmid, permitting constitutive synthesis of the lectin fusion protein in *S. dublin*, which is then administered as an oral vaccine (by the method of Brey et al, abstract #66, Program of the 27th ICAAC, N.Y., N.Y.).

In another example, the DNA encoding the lectin protein is inserted into the DNA of vaccinia virus making a recombinant virus, which is injected in the host to produce the production of antibodies specific to the lectin protein (see Moss et al Nature 311:67).

While the invention has been described with reference to specific embodiments, modifications and substitutions may be made without departing from the scope of the invention defined in the following claims.

We claim:

1. The process of immunizing against *Entamoeba histolytica* comprising
   using 170K Dalton purified galactose specific lectin protein of *E. histolytica* in vaccinating the host with the vaccine, eliciting a host immune response against the vaccine, and immunizing the host against invasive amebiasis by *E. histolytica* trophozoites.

2. The process of claim 1 wherein the using 170K Dalton purified galactose specific lectin protein comprises using a portion of the purified lectin protein molecules.

3. The process of claim 1 wherein the using 170K Dalton purified galactose specific lectin protein comprises using all of the lectin protein molecules.

4. The process of claim 1 wherein the using 170K Dalton purified galactose specific lectin protein comprises inserting the DNA, encoding the lectin protein into a DNA virus vector or an attenuated bacteria, and producing a recombinant virus.

5. A vaccine for immunizing comprising a 170K Dalton purified galactose specific lectin protein of *E. histolytica*.

* * * * *

UNITED STATES PATENT AND TRADEMARK OFFICE
CERTIFICATE OF CORRECTION

PATENT NO.     : 5,004,608
DATED          : April 2, 1991
INVENTOR(S)    : William Petri, Jr. et al.

It is certified that error appears in the above-identified patent and that said Letters Patent is hereby corrected as shown below:

Column 1,
Line 3, the following paragraph is inserted immediately after the title:

-- U.S. Government Rights
This invention was made with United States Government support under Grant No. AI 18841, awarded by the National Institutes of Health. The United States Government has certain rights in the invention. --

Signed and Sealed this

Sixteenth Day of July, 2002

Attest:

Attesting Officer

JAMES E. ROGAN
*Director of the United States Patent and Trademark Office*